United States Patent
Wettstein

(10) Patent No.: US 6,794,410 B2
(45) Date of Patent: Sep. 21, 2004

(54) USE OF (Z)-2-CYANO-3-HYDROXY-BUT-2-ENOIC ACID-(4'-TRIFLUOROMETHYLPHENYL)-AMIDE FOR TREATING MULTIPLE SCLEROSIS

(75) Inventor: Joseph Wettstein, Lebanon, NJ (US)

(73) Assignee: Aventis Pharmaceuticals Inc., Bridgewater, NJ (US)

(*) Notice: Subject to any disclaimer, the term of this patent is extended or adjusted under 35 U.S.C. 154(b) by 14 days.

(21) Appl. No.: 10/113,078

(22) Filed: Apr. 1, 2002

(65) Prior Publication Data

US 2002/0177623 A1 Nov. 28, 2002

Related U.S. Application Data

(60) Provisional application No. 60/281,685, filed on Apr. 5, 2001.

(30) Foreign Application Priority Data

Oct. 2, 2001 (GB) .............................................. 0123571

(51) Int. Cl.$^7$ ............................................ A61K 31/275
(52) U.S. Cl. ..................................................... 514/521
(58) Field of Search ................................. 514/521, 523

(56) References Cited

U.S. PATENT DOCUMENTS

| | | | |
|---|---|---|---|
| 4,061,767 A | * 12/1977 | Ertel et al. ................... | 514/466 |
| 4,087,535 A | * 5/1978 | Heubach ...................... | 514/378 |
| 4,284,784 A | * 8/1981 | Ho .............................. | 548/146 |
| 4,284,786 A | 8/1981 | Kammerer et al. | |
| 4,351,841 A | * 9/1982 | Kammerer et al. ......... | 514/378 |
| 4,965,276 A | 10/1990 | Bartlett et al. | |
| 4,965,278 A | * 10/1990 | Horwell et al. ............. | 514/414 |
| 5,268,382 A | 12/1993 | Bartlett et al. | |
| 5,459,163 A | * 10/1995 | Bartlett et al. ............... | 514/378 |
| 5,679,709 A | 10/1997 | Bartlett et al. | |
| 5,714,514 A | 2/1998 | Kämmerer et al. | |
| 5,780,592 A | 7/1998 | Müllner et al. | |
| 5,856,330 A | 1/1999 | Müllner et al. | |
| 5,981,536 A | 11/1999 | Müllner et al. | |
| 5,990,141 A | 11/1999 | Hirth et al. | |
| 6,011,051 A | 1/2000 | Müllner et al. | |
| 6,060,494 A | 5/2000 | Faasch et al. | |
| 6,133,301 A | 10/2000 | Bartlett | |
| 2002/0006945 A1 | 1/2002 | Bartlett et al. | |
| 2002/0022646 A1 | * 2/2002 | Avrutov et al. .............. | 514/378 |

FOREIGN PATENT DOCUMENTS

| | | |
|---|---|---|
| EP | 0896537 | 8/1999 |
| WO | 9318776 | 9/1993 |
| WO | 9424095 | 10/1994 |
| WO | 0033876 | 6/2000 |

OTHER PUBLICATIONS

Menor et al, J. Pharm. Soc. Wisconsin, pp. 33–38, 1999.*
Arvana Tablets, Prescription information, Apr. 2002.*
Schorlemmer H.U. et al., Treatment of Acute And Chronic Relapsing Experimental Allergic Encephalomyelitis (EAE) By The Malononitrilamides MNA 279 and MNA 715, Int J. Tissue React (1997, pp. 64, vol. 19, No. 1–2), abstract 73.
Bertolini, Giorgio et al., A New Rational Hypothesis for the Pharmacophore of the Active Metabolite of Leflunomide, a Potent Immunosuppresive Drug, J. Med. Chem. 1997, pp. 2011–2016, vol. 40.
Kaplan, Mariana J., Leflunomide Aventis Pharma, Current Opinion in investigation Drugs 2001 pp. 222–230 vol. 2(2).
Miljkovic, Dj. et al., Leflunomide Inhibits Activation of Inducible Nitric Oxide Synthase in Rat Astrocytes, Brain Research (2001) pp. 331–338, vol. 889.
C. Bolton, "Recent Advances in the Pharmacological Control of Experimental Allergic Encephalomyelitis (EAE) and the Implications for Multiple Sclerosis Treatment", (1995), Multiple Sclerosis, vol. 1, pp. 143–149.
Amitabh Prakash, et al., "Leflunomide, A Review of its Use in Active Rheumatoid Arthritis", (1999), Drugs, vol. 58 (6), pp. 1137–1164.
J.M. Bruneau, et al., "Purification of Human Dihydro–Orotate Dehydrogenase and Its Inhibition by A77 1726, the Active Metabolite of Leflunomide", Biochem. J. (1998), vol. 336, pp. 299–303.
Raymond D. Adams, et al., "Multiple Sclerosis and Allied Demyelinating Diseases", in Principles of Neurology, (1997), pp. 902–921, McGraw–Hill, New York.
Anthony S. Fauci, et al., "Mutliple Sclerosis and Other Demyelinating Disease", in Harrison's Principles of Internal Medicine, 14$^{th}$ Edition, (1994), vol. 2, pp. 2409–2419, McGraw–Hill, New York.
Holly M. Cherwinski, et al., "The Immunosuppressant Leflunomide Inhibits Lymphocyte Progression Through Cell Cycle by a Novel Mechanism", (1995),J. Pharmacol. Exp. Therap., vol. 272 (1), pp. 460–468.

* cited by examiner

Primary Examiner—James H Reamer
(74) Attorney, Agent, or Firm—Joseph Strupczewski; Balaram Gupta

(57) ABSTRACT

The invention relates to the use of compound of Formula I in treating patients for the symptoms of multiple sclerosis.

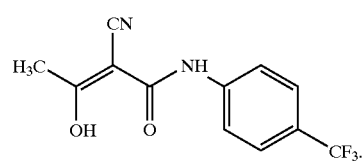

Formula I

1 Claim, 1 Drawing Sheet

USE OF (Z)-2-CYANO-3-HYDROXY-BUT-2-ENOIC ACID-(4'-TRIFLUOROMETHYLPHENYL)-AMIDE FOR TREATING MULTIPLE SCLEROSIS

This application claims the benefit of U. S. Provisional Application No. 60/281,685 filed Apr. 5, 2001 and Great Britain application No. 0123571.2, filed Oct. 2, 2001.

FIELD OF THE INVENTION

The present invention relates to methods of treating multiple sclerosis. In particular, the present invention relates to the treatment of multiple sclerosis with (Z)-2-cyano-3-hydroxy-but-2-enoic acid-(4'-trifluoromethylphenyl)-amide, commonly known as teriflunomide.

BACKGROUND OF THE INVENTION (Z)-2-cyano-3-hydroxy-but-2-enoic acid-(4'-trifluoromethylphenyl)-amide (teriflunomide) has the structure illustrated in Formula I:

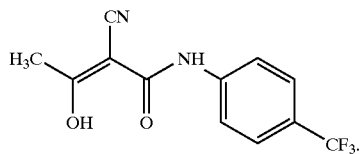

Formula I

It is an active metabolite of the disease-modifying, antirheumatic drug 5-methylisoxazole-4-carboxylic-(4-trifluoromethyl)-anilide commonly known as leflunomide, the structure of which is shown in Formula II. Leflunomide was first disclosed generically in U.S. Pat. No. 4,087,535, issued on May 2, 1978 and specifically in U.S. Pat. No. 4,284,786, issued on Aug. 18, 1981, wherein it was disclosed that the compound could be used for the treatment of multiple sclerosis. The aforementioned patents are both incorporated herein by reference.

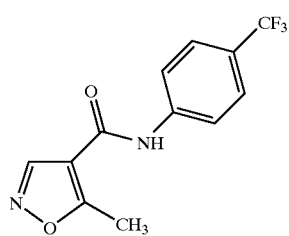

Formula II (Z)-2-cyano-3-hydroxy-but-2-enoic acid-(4'-trifluoromethylphenyl)-amide (teriflunomide,Formula I) use in treating chronic graft-versus-host disease has been disclosed in U.S. Pat. No. 4,965,276 issued on Oct. 23, 1990, incorporated herein by reference. U.S. Pat. No. 5,459,163 issued on Oct. 21, 1997 and U.S. Pat. No. 5,679,709 issued on Oct. 21, 1997 disclose compositions useful for treating autoimmune diseases in particular lupus erythematosus. Both of the aforementioned patents are incorporated herein by reference. Teriflunomide has been shown to produce antiproliferative effects on a wide variety of immune cells and cell lines (Cherwinski H. M., et al., J Pharmacol. Exp. Ther. 1995;272:460–8; Prkash A., et al., Drugs 1999;58(6): 1137–66; Bartlett R. R. et al., Agent Action 1991;32(1–2): 10–21). Additionally, it inhibits the enzyme dihydrooate dehydrogenase, an enzyme essential for the synthesis of pyrimidines (Bruneau J-M, et al., Biochem. J. 1998; 36:299–303).

Multiple sclerosis (MS) is a debilitating, inflammatory, neurological illness characterized by demyelination of the central nervous system. The disease primarily affects young adults with a higher incidence in females. Symptoms of the disease include fatigue, numbness, tremor, tingling, dysesthesias, visual disturbances, dizziness, cognitive impairment, urologic dysfunction, decreased mobility, and depression. Four types classify the clinical patterns of the disease: relapsing-remitting, secondary progressive, primary-progressive and progressive-relapsing (S. L. Hauser and D. E. Goodkin, Multiple Sclerosis and Other Demyelinating Diseases in Harrison's Principles of Internal Medicine $14^{th}$ Edition, vol. 2, Mc Graw-Hill, 1998, pp. 2409–2419).

The exact etiology of MS is unknown; however, it is strongly suspected that the demyelination characteristic of the disease is the result of an autoimmune response perhaps triggered by an environmental insult, e.g. a viral infection. Specifically, it is hypothesized that MS is caused by a T-cell-mediated, autoimmune inflammatory reaction. The autoimmune basis is strongly supported by the fact that antibodies specific to myelin basic protein (MBP) have been found in the serum and cerebrospinal fluid of MS patients and these antibodies along with T-cells that are reactive to MBP and other myelin proteolipids increase with disease activity. Furthermore, at the cellular level it is speculated that T-cell proliferation and other cellular events, such as activation of B cells and macrophages and secretion of cytokines accompanied by a breakdown of the blood-brain barrier can cause destruction of myelin and oligodendrocytes. (R. A. Adams, M. V. Victor and A. H. Ropper eds, Principles of Neurology, Mc Graw-Hill, New York, 1997, pp.903–921). Progressive MS (primary and secondary may be based on a nuerodegenerative process occurring with demyelination.

At the present time there is no cure for MS. Current therapies are aimed at alleviating the symptoms of the disease and arresting its progress, as much as possible. Depending upon the type, drug treatment usually entails the use of disease-modifying agents such as the interferons (interferon beta 1-a, beta 1-b and alpha 2), glatiramer acetate or corticosteroids such as methylprednisolone and prednisone. Also, chemotherapeutic agents such as methotrexate, azathioprine, cladribine cyclophosphamide and cyclosporine have been used. All of the above treatments have side-effect liabilities, little or no effect on fatigue and depression, limited effects on relapse rates and on ability to prevent exacerbation of the disease. Treatment with interferons may also induce the production of neutralizing antibodies, which may ultimately decrease the efficacy of this therapy. Therefore, there still exists a strong need for new drugs, which can be used alone or in combination with other drugs to combat the progression and symptoms of MS.

SUMMARY OF THE PRESENT INVENTION

The present invention is a method of treating multiple sclerosis in patients by administering a compound of Formula I or a pharmaceutically acceptable salt thereof, in a therapeutically effective amount to treat the disease. The present invention also comprises a method of treating multiple sclerosis in patients by administering a combination of a compound of Formula I or a pharmaceutically acceptable salt thereof, with another compound known to be effective for the treatment of multiple sclerosis in therapeutically effective amounts to treat the disease.

DETAILED DESCRIPTION OF THE INVENTION

Terms used herein have the meanings defined in this specification.

a) "Pharmaceutically acceptable salts" means either an acid addition salt or a basic addition salt, whichever is possible to make with the compounds of the present invention. "Pharmaceutically acceptable acid addition salt" is any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula I. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection of the appropriate salt may be important so that the ester is not hydrolyzed. The selection criteria for the appropriate salt will be known to one skilled in the art.

b) "Patient" means a warm blooded animal, such as for example rat, mice, dogs, cats, guinea pigs, and primates such as humans.

c) "Treat" or "treating" means any treatment, including, but not limited to, alleviating symptoms, eliminating the causation of the symptoms either on a temporary or permanent basis, or preventing or slowing the appearance of symptoms and progression of the named disorder or condition.

d) "Therapeutically effective amount" means an amount of the compound, which is effective in treating the named disorder or condition.

e) "Pharmaceutically acceptable carrier" is a non-toxic solvent, dispersant, excipient, adjuvant or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

f) "Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

g) "Leflunomide" is the generic name for 5-methylisoxazole-4-carboxylic-(4-trifluoromethyl)-anilide.

h) "Teriflunomide" is the generic name for (Z)-2-cyano-3-hydroxy-but-2-enoic acid-(4'-trifluoromethylphenyl)-amide.

The synthesis of the compound of Formula 1 has been disclosed, and is accomplished by methods that are well known to those skilled in the art. For example, U.S. Pat. No. 5,504,084, issued on Apr. 2, 1996, and U.S. Pat. No. 5,990,141, issued on Nov. 23, 1999 disclose methods of synthesis. The aforementioned patents are incorporated herein by reference. One synthesis as disclosed in U.S. Pat. No. 5,990,141 is illustrated in Scheme 1.

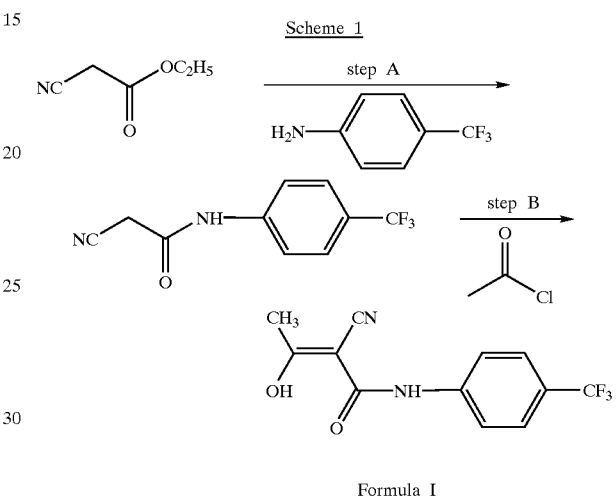

Formula I

In Scheme 1, step A commercially available cyanoacetic acid ethyl ester is reacted with commercially available 4-trifluoromethylaniline neat at elevated temperature to give cyanoacet-(4-trifluoromethyl)anilide. In step B, the product from step A is dissolved in tetrahydrofuran and reacted with NaH in acetonitrile followed by reaction with acetyl chloride to produce the compound of Formula I.

One method of showing the utility of the present compound as a pharmaceutical that may be useful for the treatment of various conditions associated with MS is its ability to inhibit effects of experimental allergic encephalomyelitis in laboratory animals.

Experimental allergic encephalomyelitis (EAE) is an animal model for MS, which entails inducing a T-cell-mediated autoimmune disease against myelin basic protein in certain susceptible mammalian species. The EAE model is an appropriate method for studying the inflammation of the brain and spinal cord associated with MS (see Bolton, C. Mult. Scler. 1995;1(3);143–9).

In treating a patient afflicted with a condition described above, a compound of Formula (I) can be administered in any form or mode which makes the compound bioavailable in therapeutically effective amounts, including orally, sublingually, buccally, subcutaneously, intramuscularly, intravenously, transdermally, intranasally, rectally, topically, and the like. One skilled in the art of preparing formulations can determine the proper form and mode of administration depending upon the particular characteristics of the compound selected for the condition or disease to be treated, the stage of the disease, the condition of the patient and other relevant circumstances. For example, see Remington's Pharmaceutical Sciences, 18th Edition, Mack Publishing Co. (1990), incorporated herein by reference.

The compound of the present invention may be administered orally, for example, in the form of tablets, troches, capsules, elixirs, suspensions, solutions, syrups, wafers, chewing gums and the like and may contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials, which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors.

The compound of Formula I of this invention may also be administered topically, and when done so the carrier may suitably comprise a solution, ointment or gel base. The base, for example, may comprise one or more of petrolatum, lanolin, polyethylene glycols, bee wax, mineral oil, diluents such as water and alcohol, and emulsifiers and stabilizers.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials.

The dosage range at which the compound of Formula I exhibits its ability to act therapeutically can vary depending upon its severity, the patient, the formulation, other underlying disease states that the patient is suffering from, and other medications that may be concurrently administered to the patient. Generally, the compound of Formula I will exhibit their therapeutic activities at dosages of between about 0.001 mg/kg of patient body weight/day to about 100 mg/kg of patient body weight/day.

All cites to publications and patents herein are hereby incorporated by reference.

Figure 1:
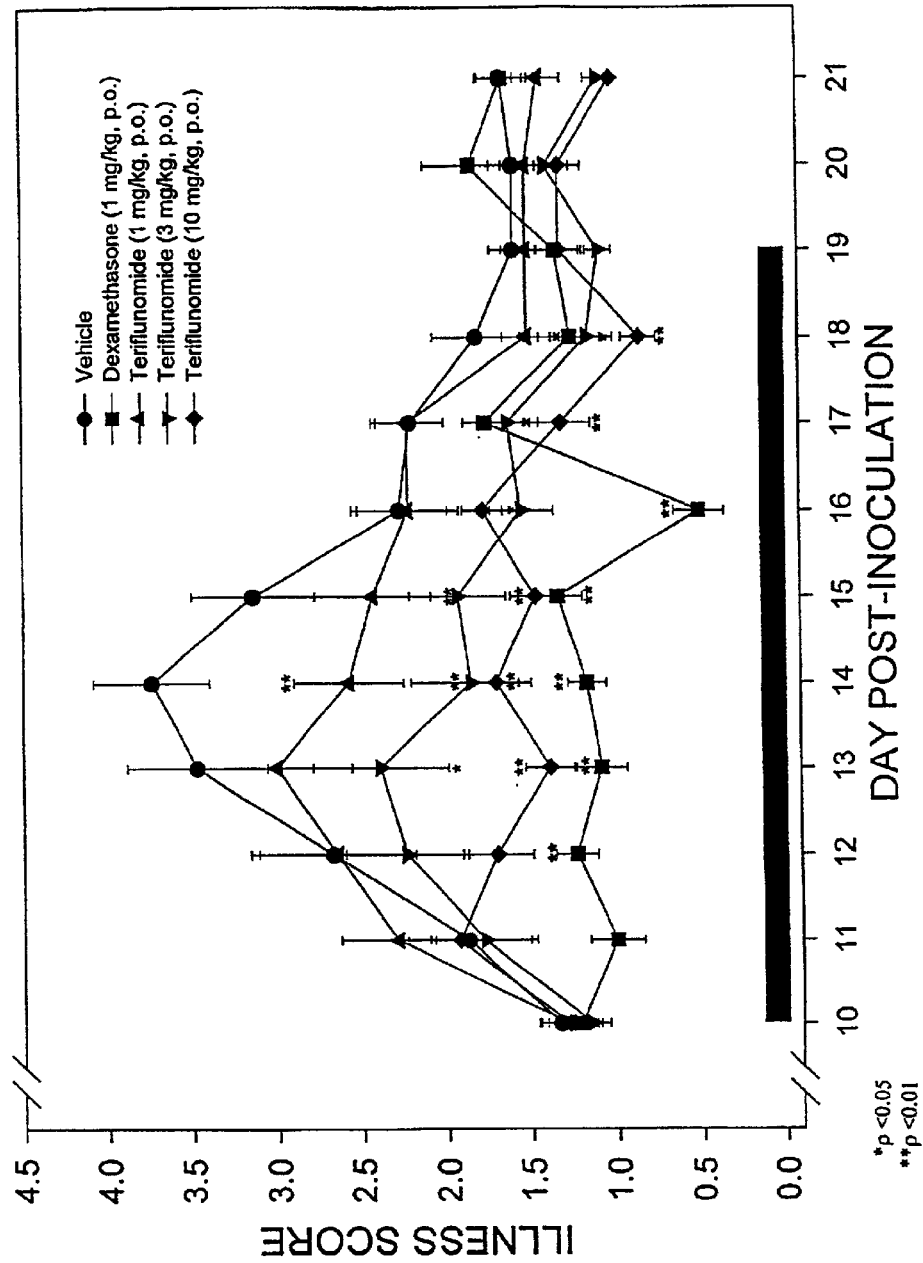
FIG. 1 shows the effect of teriflunomide on symptoms in the Rat Experimental Allergic Encephalomyelitis (EAE) at 3 different doses when administered orally (p.o.) as compared to vehicle and dexamethasone.

The following example is being presented to further illustrate the invention. However, it should not be construed as limiting the invention in any manner.

EXAMPLE

Rat Experimental Allergic Encephalomyelitis (Rat EAE)

Experimental allergic encephalomyelitis (EAE) is a T-cell-mediated autoimmune disease of the nervous system that develops in susceptible animals following sensitization with either whole spinal cord homogenate or a component (myelin basic protein). The EAE rodent model is an appropriate tool for studying the inflammation of the brain and spinal cord observed in MS patients. In rodents, injection of whole spinal cord or spinal cord components such as myelin basic protein induces an autoimmune response based on the activation of T-lymphocytes. Clinical disease typically becomes manifest around day 8–10 after inoculation, observed as a broad spectrum of behavioral anomalies ranging from mild gait disturbances and tail atony to complete paralysis and death. Weight loss typically occurs. In animals that survive, spontaneous recovery occurs, accompanied by variable recovery of most motor function. Depending on the species, allergen, and methodology used, animals tested by the EAE model may experience a single (acute EAE) or several (chronic relapsing EAE) attacks. Several treatment paradigms may be used: the drug or treatment of choice may be administered before immunization, during the nonsymptomatic period or during the clinical disease.

Animals:
  Female Lewis rats, 160–220 g (Charles River)
Antigen:
  Whole Guinea Pig spinal cord (Harlan Biosciences).
  Complete Freund's adjuvant H37 Ra [1 mg/ml Mycobacterium Tuberculosis H37 Ra] (Difco).
Additional antigen:
  Mycobacterium Tuberculosis (Difco).
  Bordetella Pertussis [Heat Killed] (Difco).

Antigen Preparation: (for Approximately 720 Animals)

1. Weigh 5 grams of frozen guinea pig spinal cord.
2. Add 5 g spinal cord to 5 ml 0.9% saline (1 g/ml) in a round bottom centrifuge tube
3. Homogenize on ice with the Tissue-tech until the tissue is completely disrupted (approximately 5 minutes).
4. Add 10 ml Complete Freund's adjuvant H37 Ra supplemented with 200 mg Mycobacterium Tuberculosis (20 mg/ml Complete Freund's adjuvant H37 Ra).
5. Extract homogenate/adjuvant from tube by sucking it into a 10 ml syringe fitted with an 18 gauge emulsifying needle.
6. Emulsify between two 30 ml glass syringes until it becomes difficult to continue passing the material through the needle. (Approximately 5 minutes {there must be no separation between the oil phase and the aqueous phase}).
7. Use immediately or keep on ice until needed (not more than 30 min) (do not freeze).

Protocol

1. Female Lewis rats (Charles River) are given free access to food and water and should be acclimated a minimum of 3 days before use in experiments.
2. Rats weighing 160 and 220 grams are initially induced with 5% isoflurane (Aerrane, Fort Dodge), 30% $O_2$, 70% $N_2O$ for 2–5 minutes.
3. The rat is then placed onto a circulating water heating blanket (Gaymar) (dorsal surface up) and into the nose cone for spontaneous respiration of anesthetic gases. The isoflurane is reduced to 2%.
4. Two subcutaneous injections (0.1 ml each) of either antigen or normal saline are made into ventral surface of the hind paws.
5. The animals are removed from the nose cone, weighed and numbered.

6. The rats are allowed to awake from anesthesia and are placed into individual cages.
7. The animals are observed daily for signs of EAE induction (see criteria below)

| STAGE: 0 | NORMAL |
|---|---|
| STAGE: 1 | Abnormal gate and tail atony |
| STAGE: 2 | Mild but definite weakness of one or both hind legs |
| STAGE: 3 | Severe weakness of one or both hind legs or mild ataxia |
| STAGE: 4 | Severe paraparesis and minimal hind leg movement |
| STAGE: 5 | No hind leg movement and paraplegia |
| STAGE: 6 | Moribund state with no spontaneous movement and impaired respiration. Increasing degree of front leg involvement and urinary and fecal incontinence may also occur |
| STAGE: 7 | DEATH |

Treatment was begun on day 10 after immunization. Since the disease symptoms in this model typically appear 10–11 days after inoculation, this time point may be considered to represent the initial phase of an acute episode of MS. It is judged that this delay of the start of treatment mimics the clinical situation more closely than the traditionally used protocols where drugs are administered at the time of, or even before, inoculation (Teitelbaum D. et al., Proc Natl Acad Sci USA 1999; 96: 3842–3847 and Brod S. A., et al., Ann Neurol 2000; 47: 127–131)

The effect of teriflunomide on symptoms of EAE in rat at various doses is illustrated in FIG. 1. Dexamethasone is included in the figure for comparison.

What is claimed is:

1. A method of treating multiple sclerosis which comprises administering to a patient having multiple sclerosis a therapeutically effective amount of a compound of Formula I, its stereoisomer, or a pharmaceutically acceptable salt thereof,

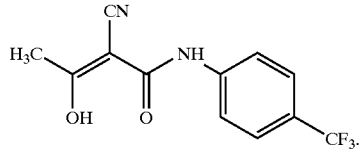

Formula I

* * * * *

(12) EX PARTE REEXAMINATION CERTIFICATE (9781st)
United States Patent
Wettstein

(10) Number: US 6,794,410 C1
(45) Certificate Issued: Jul. 31, 2013

(54) USE OF (Z)-2-CYANO-3-HYDROXY-BUT-2-ENOIC ACID-(4'-TRIFLUOROMETHYLPHENYL)-AMIDE FOR TREATING MULTIPLE SCLEROSIS

(75) Inventor: Joseph Wettstein, Lebanon, NJ (US)

(73) Assignee: Aventis Pharmaceuticals Inc., Bridgewater, NJ (US)

Reexamination Request:
No. 90/011,959, Oct. 14, 2011

Reexamination Certificate for:
Patent No.: 6,794,410
Issued: Sep. 21, 2004
Appl. No.: 10/113,078
Filed: Apr. 1, 2002

Related U.S. Application Data

(60) Provisional application No. 60/281,685, filed on Apr. 5, 2001.

(30) Foreign Application Priority Data

Oct. 2, 2001 (GB) .................................. 0123571

(51) Int. Cl.
*A61K 31/277* (2006.01)
*A61K 31/275* (2006.01)

(52) U.S. Cl.
USPC .......................................................... 514/521

(58) Field of Classification Search
None
See application file for complete search history.

(56) References Cited

To view the complete listing of prior art documents cited during the proceeding for Reexamination Control Number 90/011,959, please refer to the USPTO's public Patent Application Information Retrieval (PAIR) system under the Display References tab.

*Primary Examiner* — Sharon Turner

(57) ABSTRACT

The invention relates to the use of compound of Formula I in treating patients for the symptoms of multiple sclerosis.

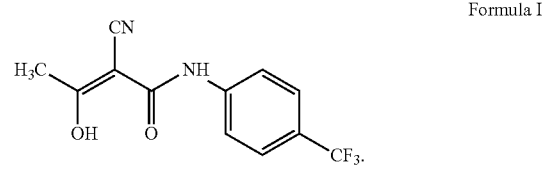

Formula I

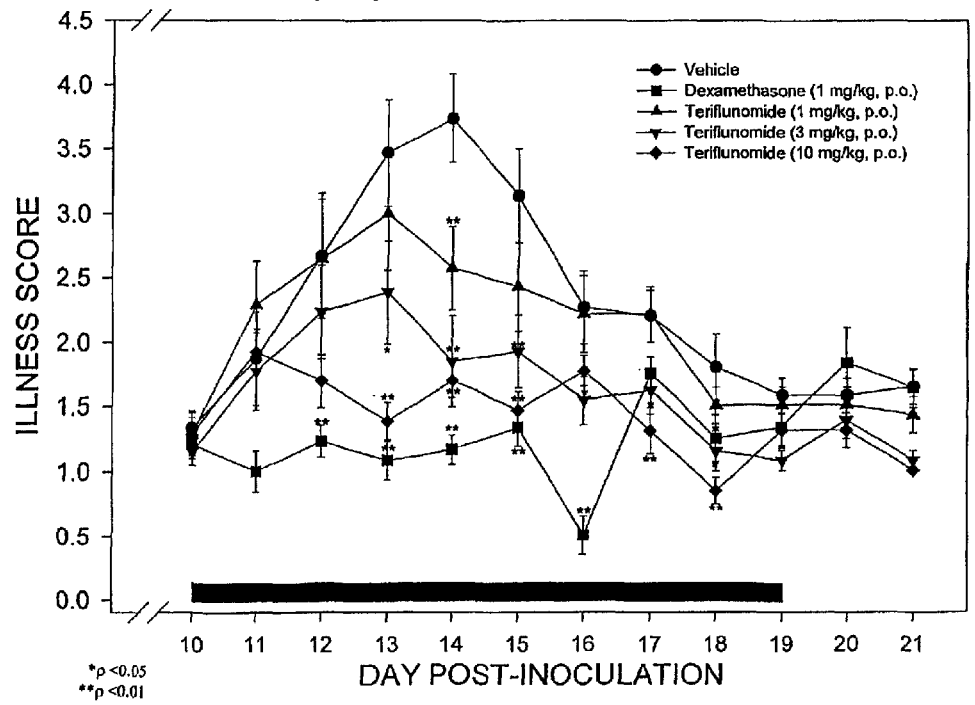

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is cancelled.

New claims 2-22 are added and determined to be patentable.

*2. A method of treating multiple sclerosis (MS) comprising orally administering to a patient that has manifested clinical disease a therapeutically effective amount of a compound of Formula I, its stereoisomer, or a pharmaceutically acceptable salt thereof, wherein the treating alleviates the symptoms of an acute episode of MS and wherein Formula I is:*

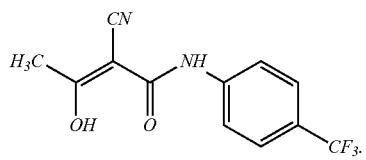

Formula I

*3. The method of claim 2, wherein the symptoms of an acute episode MS are one or more symptoms selected from the group consisting of fatigue, numbness, tremor, tingling, dysesthesias, visual disturbances, dizziness, cognitive impairment, urologic dysfunction, decreased mobility, and depression.*

*4. The method of claim 2, comprising orally administering a therapeutically effective amount of a compound of Formula I, wherein Formula I is:*

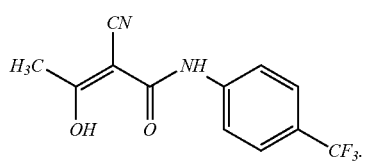

Formula I

*5. A method of treating multiple sclerosis (MS) comprising orally administering to a patient that has manifested clinical disease a therapeutically effective amount of a compound of Formula I, its stereoisomer, or a pharmaceutically acceptable salt thereof, wherein the treating slows the appearance of symptoms of an acute episode of MS, and wherein Formula I is:*

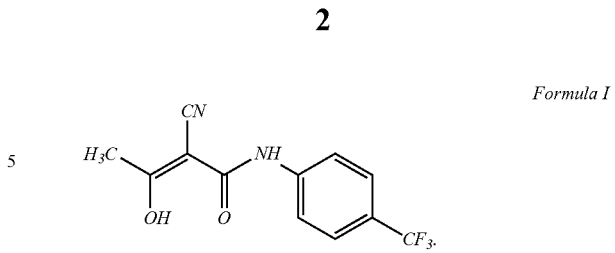

Formula I

*6. The method of claim 5, wherein the symptoms of an acute episode of MS are one or more symptoms selected from the group consisting of fatigue, numbness, tremor, tingling, dysesthesias, visual disturbances, dizziness, cognitive impairment, urologic dysfunction, decreased mobility, and depression.*

*7. The method of claim 5, comprising orally administering a therapeutically effective amount of a compound of Formula I, wherein Formula I is:*

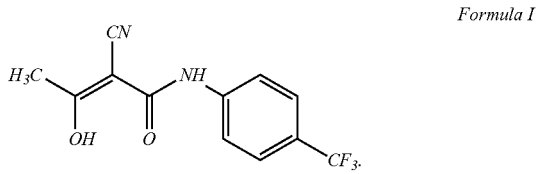

Formula I

*8. A method of treating multiple sclerosis (MS) comprising orally administering a therapeutically effective amount of a compound of Formula I, its stereoisomer, or a pharmaceutically acceptable salt thereof to a patient that has manifested clinical disease, wherein the treating slows the progression of an acute episode of MS, and wherein Formula I is:*

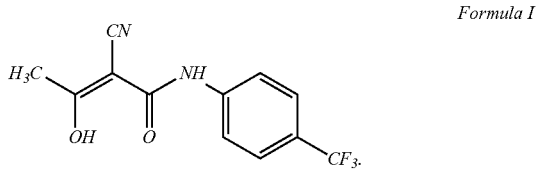

Formula I

*9. The method of claim 8, comprising orally administering a therapeutically effective amount of a compound of Formula I, wherein Formula I is:*

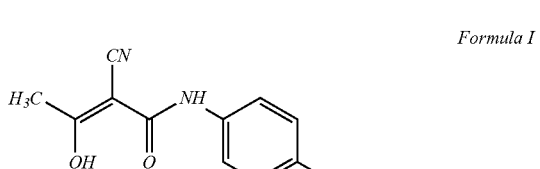

Formula I

*10. A method of treating multiple sclerosis which comprises orally administering to a patient that has manifested clinical disease a therapeutically effective amount of a compound of Formula I, its stereoisomer, or a pharmaceutically acceptable salt thereof,*

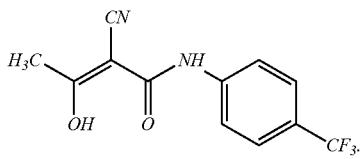

Formula I

11. The method of claim 2, wherein the compound of Formula I is formulated as teriflunomide in the presence of a pharmaceutically acceptable carrier.

12. The method of claim 5, wherein the compound of Formula I is formulated as teriflunomide in the presence of a pharmaceutically acceptable carrier.

13. The method of claim 8, wherein the compound of Formula I is formulated as teriflunomide in the presence of a pharmaceutically acceptable carrier.

14. The method of claim 10, wherein the compound of Formula I is formulated as teriflunomide in the presence of a pharmaceutically acceptable carrier.

15. The method of claim 2, wherein the therapeutically effective amount of a compound of Formula I, its stereoisomer, or a pharmaceutically acceptable salt thereof is formulated for oral administration in the form of a tablet.

16. The method of claim 15, wherein the tablet comprises one or more of a microcrystalline cellulose binder, a lactose excipient, a corn starch disintegrating agent, a magnesium stearate lubricant, or an enteric coating agent.

17. The method of claim 5, wherein the therapeutically effective amount of a compound of Formula I, its stereoisomer, or a pharmaceutically acceptable salt thereof is formulated for oral administration in the form of a tablet.

18. The method of claim 17, wherein the tablet comprises one or more of a microcrystalline cellulose binder, a lactose excipient, a corn starch disintegrating agent, a magnesium stearate lubricant, or an enteric coating agent.

19. The method of claim 8, wherein the therapeutically effective amount of a compound of Formula I, its stereoisomer, or a pharmaceutically acceptable salt thereof is formulated for oral administration in the form of a tablet.

20. The method of claim 19, wherein the tablet comprises one or more of a microcrystalline cellulose binder, a lactose excipient, a corn starch disintegrating agent, a magnesium stearate lubricant, or an enteric coating agent.

21. The method of claim 10, wherein the therapeutically effective amount of a compound of Formula I, its stereoisomer, or a pharmaceutically acceptable salt thereof is formulated for oral administration in the form of a tablet.

22. The method of claim 21, wherein the tablet comprises one or more of a microcrystalline cellulose binder, a lactose excipient, a corn starch disintegrating agent, a magnesium stearate lubricant, or an enteric coating agent.

* * * * *